United States Patent
Fuchs

(10) Patent No.: US 10,497,109 B2
(45) Date of Patent: Dec. 3, 2019

(54) TIME-LAPSE INFRARED THERMOGRAPHY SYSTEM AND METHOD FOR DAMAGE DETECTION IN LARGE-SCALE OBJECTS

(71) Applicant: Fuchs Consulting, Inc., Leesburg, VA (US)

(72) Inventor: Paul A. Fuchs, Leesburg, VA (US)

(73) Assignee: Fuchs Consulting, Inc., Leesburg, VA (US)

(*) Notice: Subject to any disclaimer, the term of this patent is extended or adjusted under 35 U.S.C. 154(b) by 0 days.

(21) Appl. No.: 15/286,779

(22) Filed: Oct. 6, 2016

(65) Prior Publication Data

US 2017/0103507 A1    Apr. 13, 2017

Related U.S. Application Data

(60) Provisional application No. 62/238,485, filed on Oct. 7, 2015.

(51) Int. Cl.
| | |
|---|---|
| *H04N 7/18* | (2006.01) |
| *G06T 7/00* | (2017.01) |
| *H04N 5/247* | (2006.01) |
| *H04N 5/33* | (2006.01) |
| *H04N 5/232* | (2006.01) |
| *H04N 5/225* | (2006.01) |
| *G01N 25/72* | (2006.01) |
| *G06K 9/00* | (2006.01) |
| *G01J 5/00* | (2006.01) |

(52) U.S. Cl.
CPC ............. *G06T 7/001* (2013.01); *G01N 25/72* (2013.01); *G06K 9/00771* (2013.01); *H04N 5/2252* (2013.01); *H04N 5/232* (2013.01); *H04N 5/23206* (2013.01); *H04N 5/247* (2013.01); *H04N 5/33* (2013.01); *G01J 2005/0081* (2013.01); *G06T 2207/10016* (2013.01); *G06T 2207/10048* (2013.01); *G06T 2207/30132* (2013.01); *G06T 2207/30184* (2013.01)

(58) Field of Classification Search
CPC ........ G01S 13/885; G01S 13/89; G01S 13/00; G01S 13/867; G01S 15/89; G01S 17/89
USPC .......................................................... 348/159
See application file for complete search history.

(56) References Cited

U.S. PATENT DOCUMENTS

| | | |
|---|---|---|
| 5,719,395 A | 2/1998 | Lesniak |
| 7,937,229 B2 | 5/2011 | Buyukozturk et al. |
| (Continued) | | |

OTHER PUBLICATIONS

D. L. Balageas et al., "Pulsed Photothermal Modeling of Layered Materials", Journal of Applied Physics, 59 (2), pp. 348-357, American Institute of Physics, Jan. 15, 1986.

(Continued)

*Primary Examiner* — Jamie J Atala
*Assistant Examiner* — Masum Billah
(74) *Attorney, Agent, or Firm* — Breiner & Breiner, L.L.C.

(57) ABSTRACT

An infrared measurement system and method including taking multiple time lapse infrared images and visual images of a large-scale object over an extended period of time and analyzing such in order to better measure internal defects are described. Data collected over extended intervals of time are processed to provide measurements which are not affected by ambient conditions and the material properties of the object. The system may include infrared camera(s), visual (video) camera(s), external sensor(s), and an embedded computer.

24 Claims, 11 Drawing Sheets

(56) References Cited

U.S. PATENT DOCUMENTS

| | | | |
|---|---|---|---|
| 7,986,218 | B2 | 7/2011 | Watters et al. |
| 8,244,485 | B2 | 8/2012 | Buyukozturk et al. |
| 8,659,661 | B2 | 2/2014 | Frank et al. |
| 8,749,635 | B2 | 6/2014 | Hogasten et al. |
| 2008/0240616 | A1* | 10/2008 | Haering ............. G06K 9/00771 382/294 |
| 2013/0176424 | A1* | 7/2013 | Weil ....................... G01S 7/003 348/128 |
| 2014/0240451 | A1* | 8/2014 | Sakano ............. G01N 21/8806 348/36 |

OTHER PUBLICATIONS

M. Omar et al., "Thermal Vision System for Protective Coat Coverage Inspection", Quantitative InfraRed Thermography Journal, vol. X, No. X/2004, pp. 1-10.

Paul A. Fuchs et al., "Thermographic Bridge Coating Inspection System", NDE/NDT for Highways and Bridges: Structural Materials Technology (SMT), 8 Pages, Aug. 21-24, 2012, New York, New York.

Paul A. Fuchs et al., "Infrared Thermographic Bridge Deck Inspection on the Poplar Street Bridge, St. Louis, Missouri", Proceedings of Structural Materials Technology VI, 8 Pages, Buffalo, New York, Sep. 2004.

Transportation Research Board, "Nondestructive Testing to Identify Concrete Bridge Deck Deterioration", Issue No. S2-R06A-RR-1, 96 Pages, 2013.

\* cited by examiner

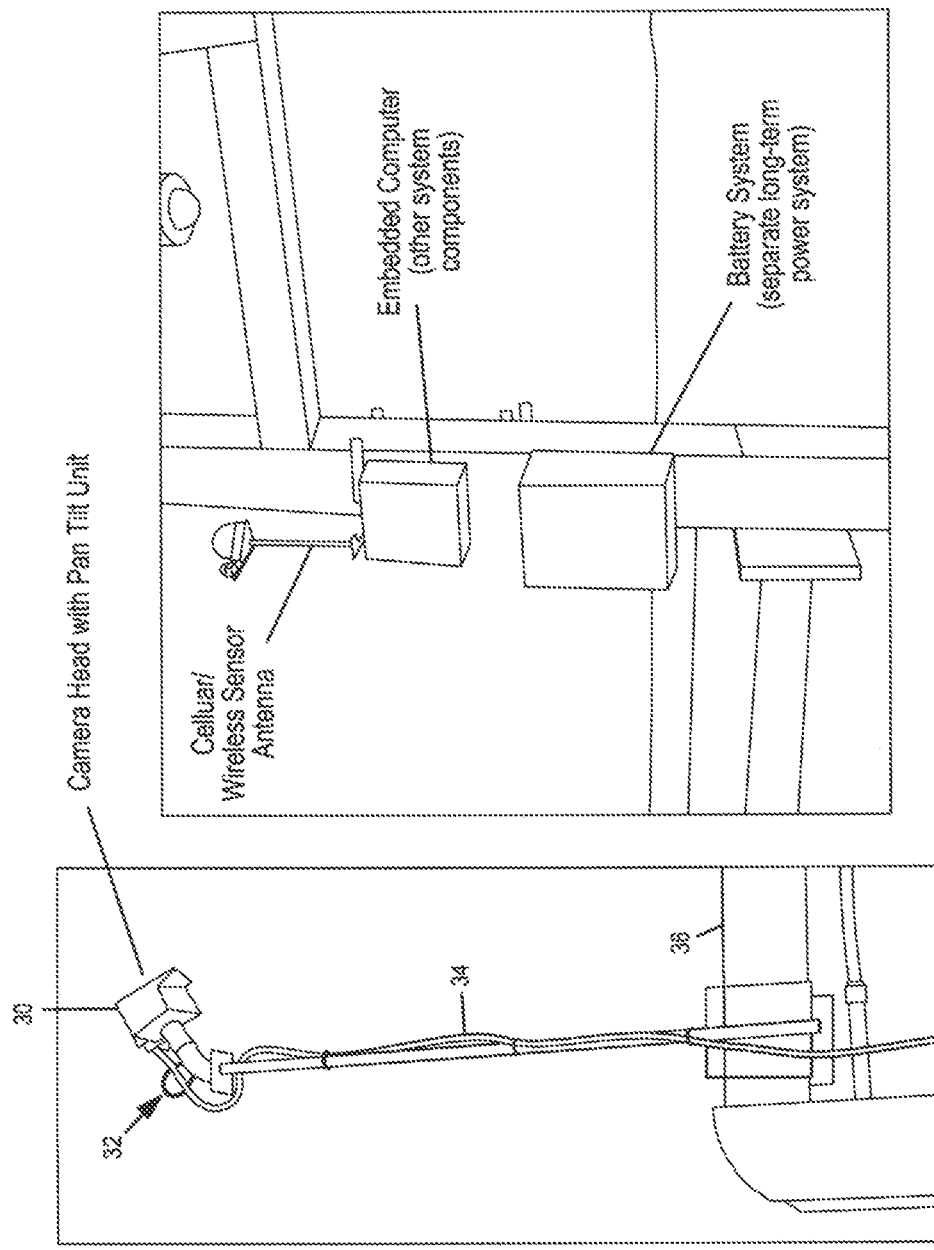

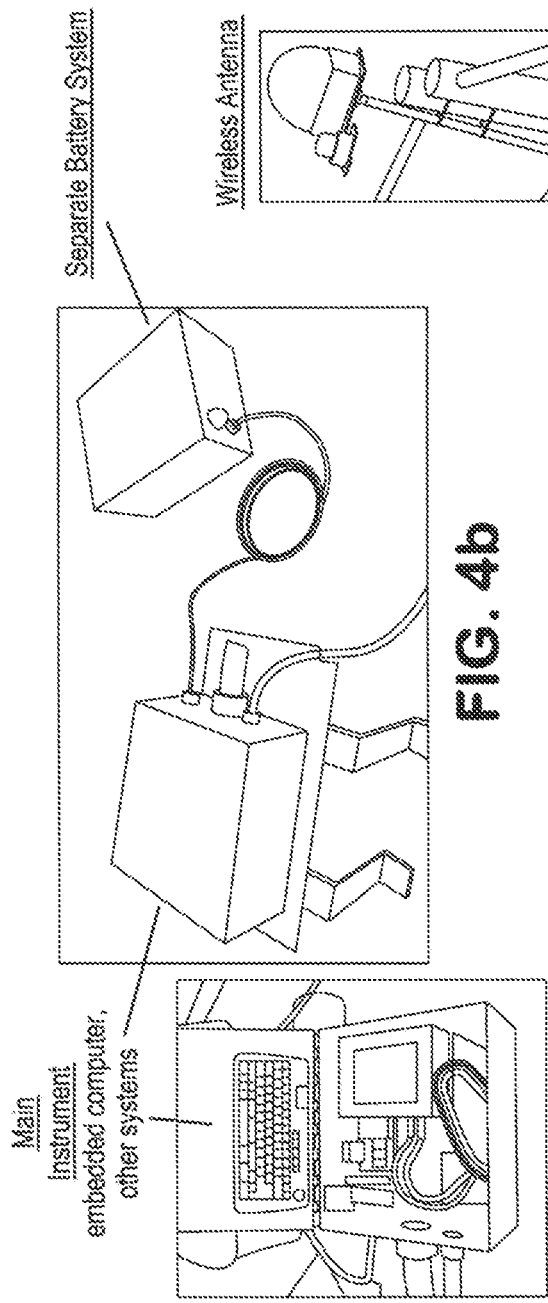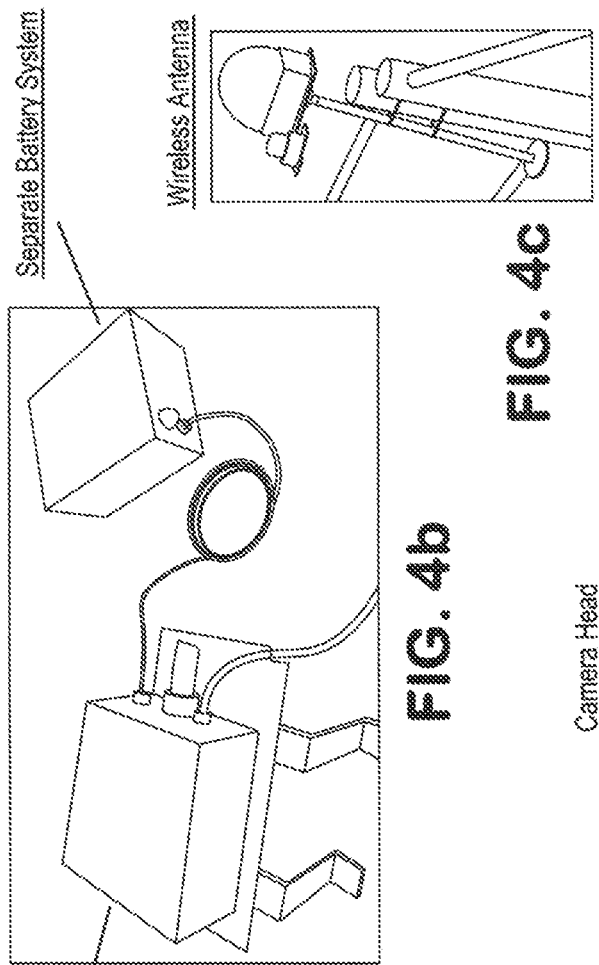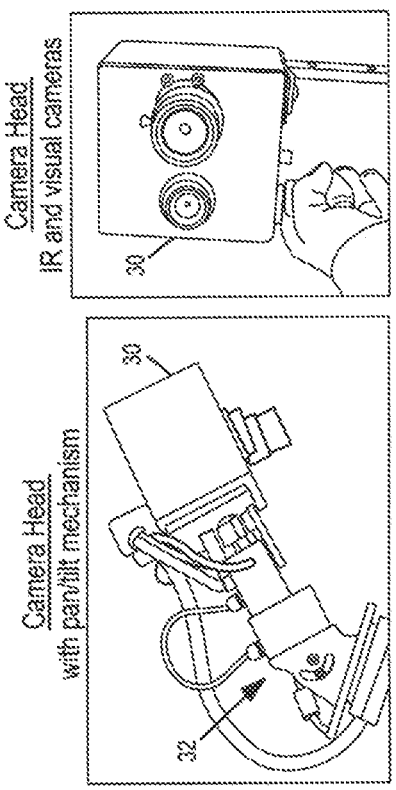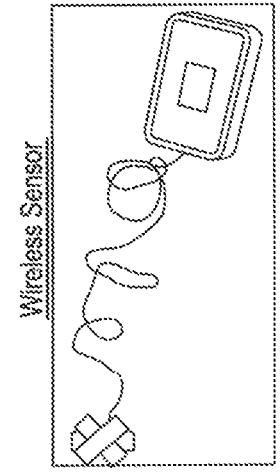

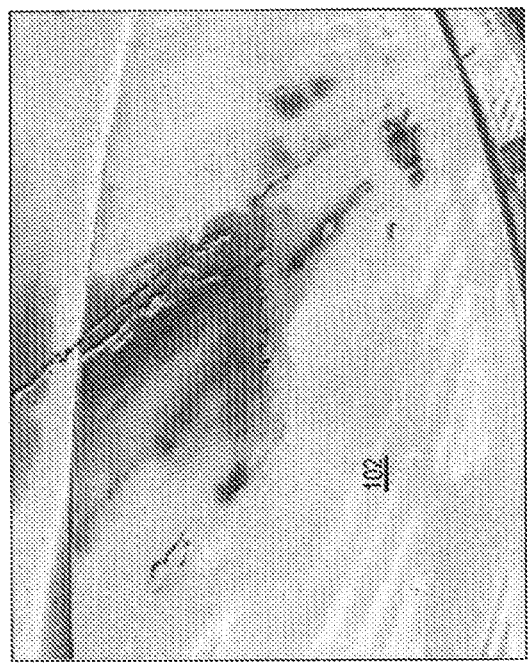
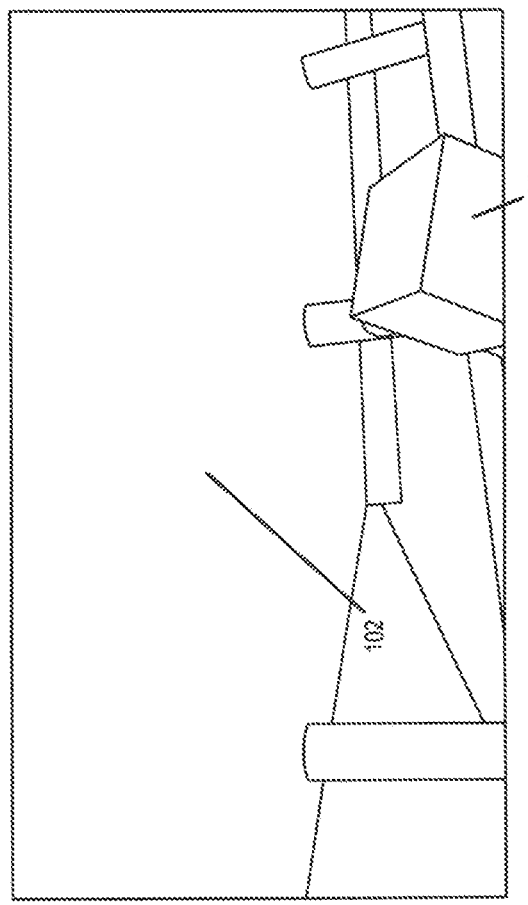
FIG. 10a
FIG. 10b

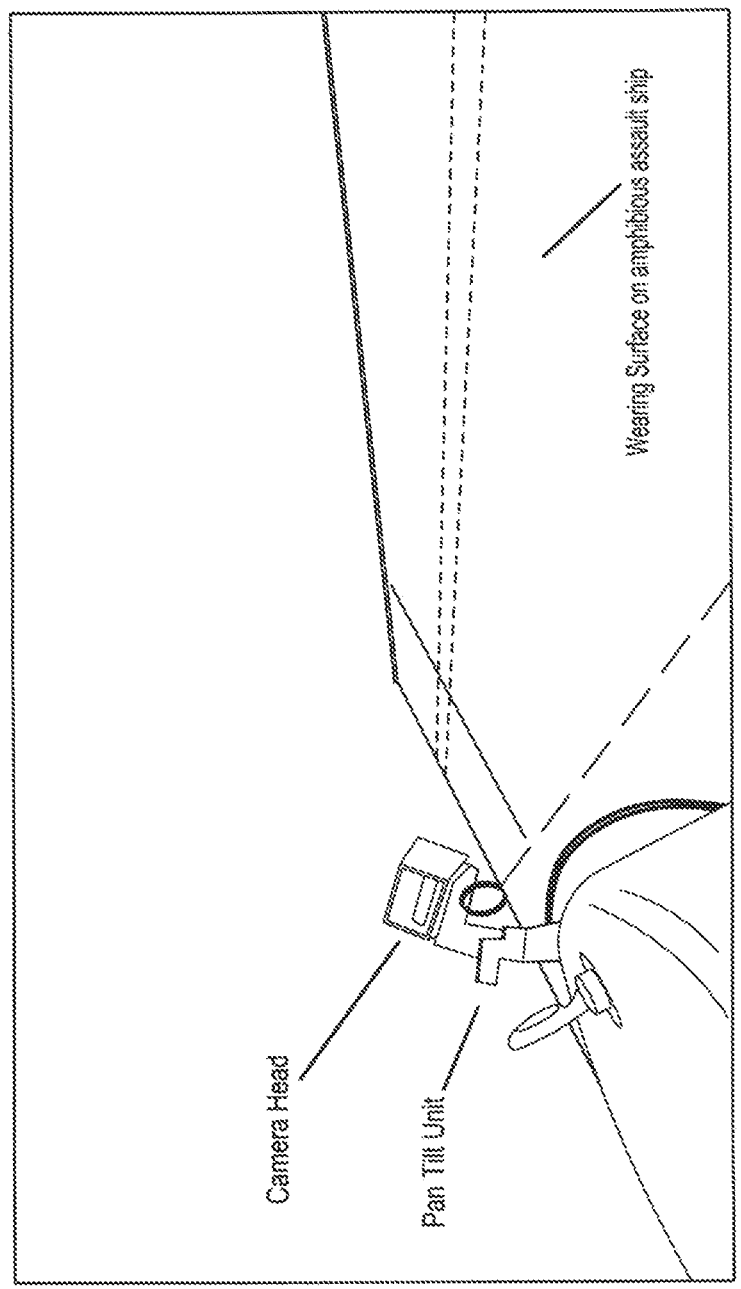

TIME-LAPSE INFRARED THERMOGRAPHY SYSTEM AND METHOD FOR DAMAGE DETECTION IN LARGE-SCALE OBJECTS

RELATED APPLICATIONS

The present application claims benefit of U.S. Provisional Application Ser. No. 62/238,485 filed Oct. 7, 2015, which is incorporated herein by reference.

FIELD OF INVENTION

The invention is directed to a system and method involving a measurement and data processing system that may be positioned on or near an object, which is substantial in size, for an extended period of time and that takes time-lapse measurements of the object in order to detect internal defects in the object. The system uses infrared thermography to monitor how heat flows through objects over an extended period of time and also monitors the surrounding environmental conditions of the object. The system includes an infrared camera, a visual camera, an embedded computer and associated components, and an environmental data collection source, preferably external sensors. The system is left in-place for a period of time imaging one or more predetermined areas of the object periodically over time. Sequences of images taken over time are processed with additional information, e.g., environmental data, in order to extract measurements of internal defects present in the object.

BACKGROUND OF THE INVENTION

The current practice of conventional infrared thermography uses infrared images taken at one instant in time in order to detect the presence of internal defects. An infrared camera is used to measure the temperature of the surface of an object and this surface temperature may vary over areas that contain an internal defect. The internal defect interrupts the flow of heat within the object, which can then be measured at the surface. This is a well-known and established measurement method.

Conventional infrared thermography, however, suffers from several limitations. First, an infrared camera does not measure temperature directly, but instead measures radiant flux emitted from an object. The radiant flux measured by the infrared camera is a function of both the temperature of an object (the quantity desired to be measured) and the emissivity of the object. It is impossible or very difficult to separate temperature variations from emissivity variations. Invalid measurements may result from this phenomenon as an infrared camera will measure two objects at the same temperature but each with different emissivity, as different temperatures.

Another limitation of conventional infrared thermography is that if measurements are not taken at the right instant in time, then a defect cannot be measured. The object needs to be measured at the proper moment in time while it is changing temperature in order to detect a defect. It is very difficult to know the optimal measurement time in advance, as this depends on a number of factors that are typically not known. As a result, many images taken with conventional infrared thermography do not show defects, even though defects are present in the object.

Conventional infrared thermography is typically performed using a hand-held camera. An operator takes images of localized sections of an object at an instant in time in order to assess the object. Conventional infrared thermography is also used on mobile platforms, such as a truck or van where an infrared camera is fixed to the vehicle and images are taken of an object as the vehicle is driven over the object (such as a bridge deck).

Active thermography has been used to better measure internal defects where a heat source is used to introduce a controlled amount of heat into an object and an infrared camera is used to monitor how the heat flows through the object. The use of the active heat source may produce increased sensitivity and greater accuracy in detection of internal defects. However, active thermography is typically used on small-scale objects and used to measure defects in objects with thin layers or near-surface defects.

Further, lock-in thermography has been used where collection of infrared images are synchronized or correlated with some external sensor data. This method seeks to correlate infrared signals with the external sensor data. This method has typically been used in laboratory systems for the measurement of small-scale objects. This method has been used to measure stress distributions in small localized areas and to find fatigue cracks in metals.

SUMMARY OF INVENTION

The invention is directed to a system and method which more accurately measures internal defects in objects, in particular large-scale objects, i.e., objects of substantial size, for example concrete structures (e.g., bridges, buildings, dams, and nuclear containment vessels), military vessels (e.g., naval vessels), and the like, wherein the system and method are useful with the object in its place of use or operation, including during use or operation thereof. Application of the system and method of the invention provides an object or structure owner (the term "object" and "structure" being used interchangeably herein) with a more accurate picture of the internal condition of a structure so that maintenance can be more optimally coordinated.

The system and method of the invention are unique in that such can measure large-scale objects and overcome the limitations of conventional infrared measurement methods. The system and method are also unique in that such can be applied to almost any structure with minimal effort. A small, self-contained system can be positioned near or on an object to be measured and the system left in-place to automatically take periodic images.

The system and method do not require an active heat source in order to better detect and quantify internal defects. Active thermography with a user supplied heat source is very difficult or impossible to provide for objects of substantial size. It is not possible to adequately provide sufficient heat for a large object, such as a concrete bridge deck, an entire building, or the flight deck of an aircraft carrier. The system and method of the invention use thermal input from the ambient environment (the sun) as opposed to a user supplied heat source. The system and method of the invention involves placement of a self-contained, small measurement system on or near an object and the taking of images of the object over time while the object experiences temperature changes from the ambient environment.

The system and method of the invention do not require an exact optimal measurement time to be known in advance. Since the system and method acquire images over an extended period of time, it is not necessary to predict the optimal measurement time as is the case for conventional infrared thermography. Conventional infrared thermography relies on imaging an object at a precise, but unknown, point in time in order to make a measurement of a defect. Conventional infrared thermography may also require disruption to the operation of an object, e.g., closing of a bridge deck to traffic in order to take measurements.

The system and method of the invention also can provide depth measurements of defects using infrared thermography on the objects analyzed. With the invention, multiple images are collected at different points in time, and data processing performed to not only by measurement detect the presence of a defect, but also measure the depth of the defect. Further, data processing can measure the rate of change of the heat flow through the object, which can better determine the depth of the defect.

The system and method of the invention can measure areas of substantial size from one fixed measurement location. The system and method can incorporate multiple camera heads, wherein a camera head can include an infrared camera alone or a camera head can include both an infrared camera and a visual camera, the latter being preferred. The multiple camera heads are linked together into one system, which can additionally incorporate a pan tilt mechanism that repositions the camera heads to different measurement positions.

The system and method of the invention can provide greater and more reliable documentation for objects or structures as compared to conventional measurements. The system and method produce a complete digital record that fully documents the spatial location of defects in an object or structure. The system and method can measure very large areas of an object or structure in one image or images.

The system and method of the invention is especially beneficial in measuring the internal condition of concrete structures. The system and method can be used on bridge decks and to measure the underside (soffit) of a bridge deck. The system and method can be used on substructure elements, such as piers, columns, pier caps, pile caps, retaining walls, or other similar elements. The system and method can be used to measure dams, nuclear containment vessels, or other structures.

The system and method of the invention is also especially beneficial in measuring buildings or other similar structures. The system and method may be used to measure external features of a building, such as windows, doors, and roof structures; or to measure internal building features, such as non-visible utilities, floor slabs, and other similar features.

The system and method of the invention is also especially beneficial in measuring the condition of thin wearing surfaces on objects, such as those found on or in military vessels. The system and method is especially useful to measure internal and external surfaces of naval vessels, e.g., the wearing surface of the flight deck of an aircraft carrier, amphibious assault ship, or similar ship.

BRIEF DESCRIPTION OF THE DRAWINGS

FIGS. 3a and 3b show a preferred embodiment of system components of the invention positioned for use to measure a highway bridge deck.

FIGS. 4a to 4f show main components for a preferred embodiment of a system of the invention, including showing a main instrument with embedded computer in an open position (FIG. 4a) and in a closed position with a battery system (FIG. 4b), wireless antenna system (FIG. 4c), pan tilt unit (FIG. 4d), camera head containing both an infrared camera and a visual camera (FIG. 4e), and wireless external sensor (FIG. 4f).

FIG. 6a shows components of the system mounted on a mast affixed to the bridge structure. FIG. 6b shows components of the system mounted on a movable (towable) mast positioned on a surface adjacent an area to be measured.

FIG. 10a shows components of the system of the invention positioned under a bridge to measure the soffit (underside) of the bridge. FIG. 10b is an infrared image provided by the system of FIG. 10a.

FIG. 11 shows a typical set-up arrangement for a system of the invention on a naval vessel, for example shown is an amphibious assault ship, for measuring a wearing surface present on the deck thereon.

DETAILED DESCRIPTION OF THE INVENTION

Figure 1:
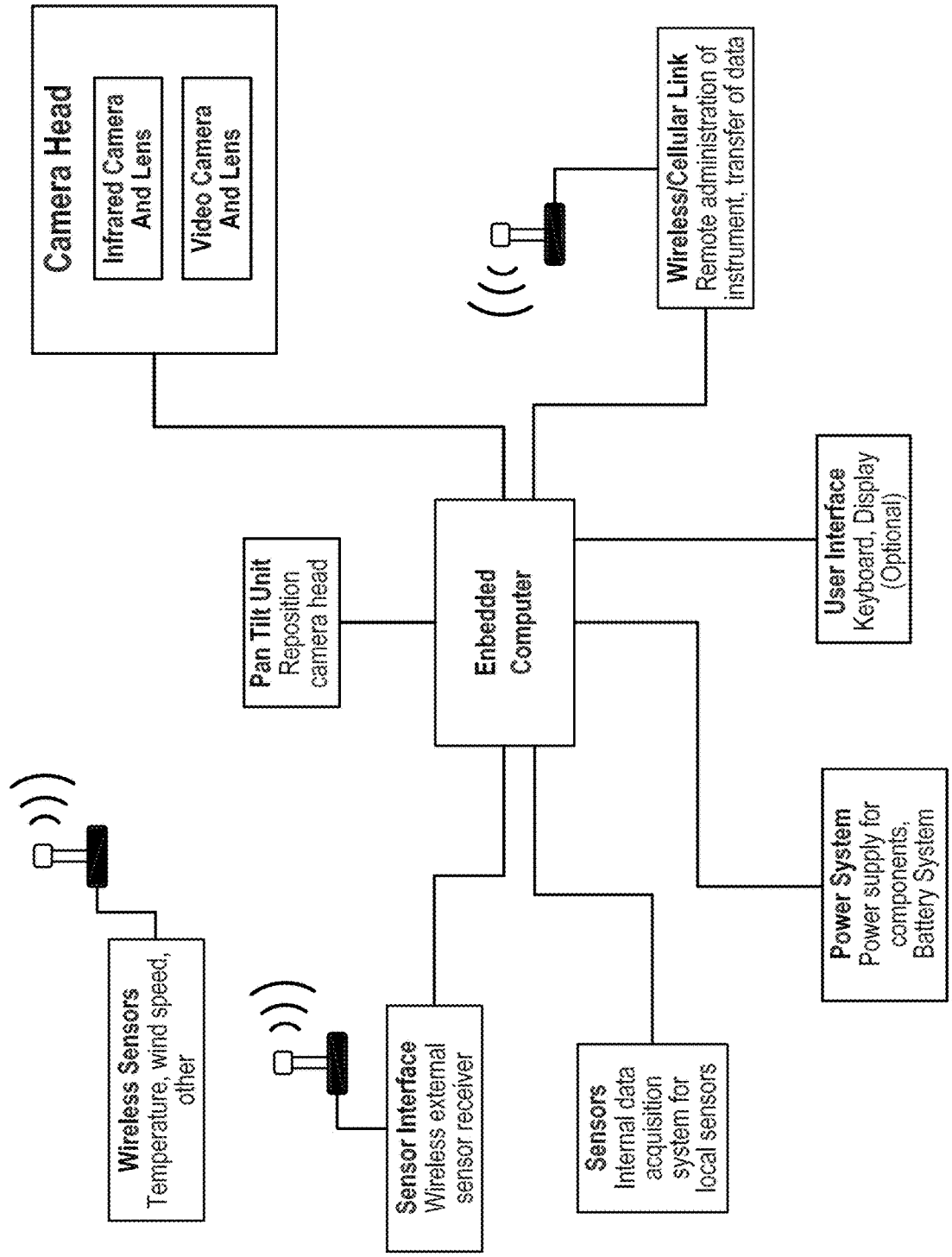
FIG. 1 is a block diagram of a preferred embodiment of hardware components of a system of the invention.

The infrared and visual measurement and data processing system of the invention is, in particular, useful for measuring objects or structures of large scale, i.e., of substantial size, to determine the location of internal defects in the objects and includes the taking of multiple infrared images and multiple visual images over an extended period of time in order to improve the detection and measurements of defects and overcome the limitations of conventional infrared thermography.

Hardware Components

Described below are hardware components of presently preferred embodiments of the invention. The primary hardware components of a preferred embodiment are shown in FIGS. 1, 3a-3b and 4a-4f, and are described in detail below. However, it is understood that other hardware components and configurations may be used without departing from the scope of the invention.

Infrared Camera and Lens

An infrared (IR) camera is used to measure radiant flux or temperature of an object. The infrared camera may use various types of lenses to optimize the field-of-view. The infrared camera may be an uncooled microbolometer-type camera, may be a cooled quantum detector camera, or may be another type of suitable system to measure thermal output.

Visual (Video) Camera and Lens

A visual or video camera is preferably incorporated into a camera head for the system containing an infrared camera such that visual images and infrared images are taken nominally for the same field-of-view of the area being analyzed. Infrared and visual images can be directly or nearly directly overlaid for comparison and analysis.

Pan Tilt Unit

A pan tilt unit may be used to reposition the camera head to multiple measurement positions from one fixed camera head installation. The pan tilt unit may be pre-programmed such that multiple orientations of the camera head can be made to provide multiple views and images thereof for automatic collection by the system at pre-defined intervals. The use of a pan tilt unit may vastly increase the measurement area at any one installation location. The system may also incorporate multiple camera heads for this purpose.

FIG. 3a shows a camera head 30 attached to a pan tilt unit 32 installed by a mounting structure on a mast 34 attached to a structural feature 36 of a bridge. FIGS. 4d and 4e show a close-up view of the camera head. FIG. 4e shows the camera head from a front view where the lens of the infrared camera and the visual camera are seen.

Embedded Computer

An embedded computer (i.e., a computer linked to the other components of the system by physical (e.g., wired) or wireless/cellular connection) or other computer system is used to collect and store images from the infrared and visual cameras. The computer can be programmed to collect images at pre-defined intervals over a specified period of time. The computer preferably controls all other system functions, including collection and storage of data from external sensors. Data processing and analysis may be performed on the embedded computer or may be performed on another external or remote computer system receiving data from the embedded computer, through physical or wireless/cellular connection.

FIGS. 4a and 4b show an example of an embedded computer as suitable for use in the system of the invention. FIG. 3b shows the embedded computer of FIGS. 4a and 4b installed on a mast on a bridge as useful in operation of the system.

Wireless/Cellular Link

An embedded wireless or cellular modem is preferably used to automatically transfer collected images to a remote site for offline data processing and/or storage. This wireless or cellular link may be used for remote system administration. The wireless or cellular modem can be part of the main instrument shown in FIG. 4a, which also holds the embedded computer, as well as other system components, such as a user interface.

User Interface

The system may be used with a user interface that may include a display monitor and a keyboard. The keyboard and display monitor may use a wireless link to the embedded computer. The embedded computer may be configured to operate without the need for the user interface components.

Sensors

Sensors may be used to collect additional information to aid in data processing. These sensors may be directly connected to the embedded computer system. Internal data acquisition system components may be needed for the directly connected sensors. Sensors may be used to collect ambient environmental data. While sensors are preferred for collecting environmental data, other environmental data collection sources may be used, such as conventional weather monitoring instruments, existing weather stations, and the like.

Additionally or alternatively, wireless sensors may be used to facilitate setup and eliminate the need to make a physical connection to one or more components of the system, such as the embedded computer. Wireless sensors are especially useful as the external sensors to monitor and record ambient environmental conditions. Examples of wireless sensor measurements are the measurement of the surface temperature of a concrete bridge deck, ambient temperature, wind speed, and solar radiation. One or more wireless sensors allow these sensors to be located physically separate from other system components and, thus, not be limited in the point of location for the sensor measurement. When a wireless sensor is used, the system will also include a sensor interface component for receiving data from the wireless sensor. The sensor interface may be a separate component or part of the embedded computer. FIG. 3b shows a wireless sensor antenna mounted on the housing containing the embedded computer and other components. FIG. 4c shows a wireless antenna mounted on a rail of a ship. FIG. 4f shows an example of a wireless sensor suitable for use as a component of the system.

Power System

The power system may be a battery system used to provide power for operation. The battery system may be internal to the main instrument containing the embedded computer or may be located in a separate enclosure. FIG. 4b shows a separate battery system connected to the main instrument including the embedded computer. FIG. 3b shows a separate battery system installed on a mast of a bridge in an operation mode, i.e., connected to the embedded computer, etc.

Calibration Specimen (Not Shown in FIG. 1)

The system may include a calibration specimen that is made from a suitable material to match the material of the object being measured and that contains internal defects of known size, depth, and spatial location. The calibration specimen may be placed within the system's field-of-view during measurements. Data measurement by the infrared camera and sensors of this calibration specimen then can be used to help calibrate measurements taken in relation to the object under analysis.

Software and Data Processing Components

Figure 2:
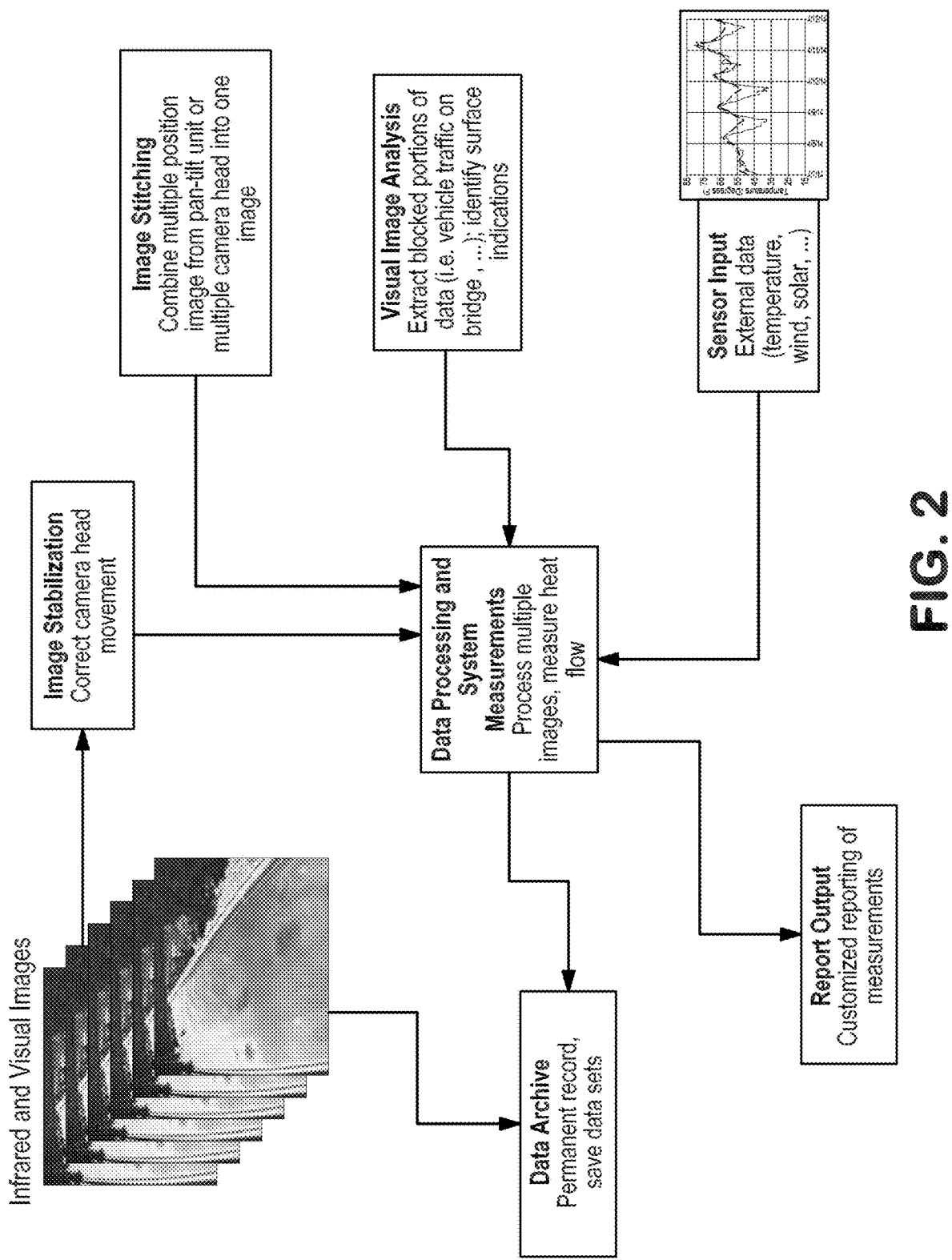
FIG. 2 is a block diagram of a preferred embodiment of software and data processing components of a system of the invention.

The system may include a unique collection of software and data processing components that can perform a combination of functions to achieve the purpose of the system and method of the invention, of which at least the following functions, as shown for example in FIG. 2, are preferred 1. Collection of simultaneous infrared images and visual images of one or more camera heads;

2. Stabilization of infrared and/or visual images to remove vibrations or unwanted movement of the camera head;

3. Stitching multiple infrared images and/or multiple visual images from multiple individual images, either from multiple camera heads or from a pan tilt unit, in order to provide a greater overall field-of-view;

4. Performing infrared image, visual image, or a combination of infrared and visual image analysis to identify surface features (e.g. patches or obstructions on the surface of an object);

5. Performing infrared image, visual image, or a combination of infrared and visual image analysis to remove periodic variations or interference in the image (e.g. traffic on a highway bridge deck or repair patch on a bridge deck);

6. Processing multiple infrared images and external sensor data to produce images of defects;

7. Performing defect recognition to determine typical defect features from other measurements;

8. Performing measurement of defect depth;

9. Performing data storage and data archiving; and

10. Creating custom data reporting of measurements.

Data Processing and System Measurement

Software components simultaneously collect data from an infrared camera(s) and a visual camera(s). Images can be collected at predetermined intervals over a specified period of time. Image collection may involve a single image or may involve multiple images collected at a very high frame rate that are then averaged or processed in some manner. The data collection system can be configured to automatically start and stop collection at operator specified times. Infrared camera image collection provides full radiometric data for measurement of radiant flux from an object.

Image Stabilization

Infrared images and visual images may be stabilized to remove potential misalignment of images due to vibrations or other unwanted movements that occur during measurement. For example, vibrations caused by movement of the camera head due to traffic on a bridge structure can be eliminated or reduced.

Stitching Multiple Images

The system can collect images from a single camera head, multiple camera heads, or camera heads with a pan tilt unit that repositions the camera head to multiple locations for measurements. When multiple images are produced, software components can stitch together, i.e., combine, these multiple images into a single composite image.

Visual Image Analysis

Software tools may examine the visual camera images as to surface features to extract surface features that need to be separated from internal defects found in processed infrared images. For example, when used on a highway bridge deck, the visual image can be used to identify the location of surface patches and these surface patches can be differentiated from internal defects.

Further, visual image analysis can be provided to detect interfering objects. Software tools can examine visual images to identify intermittent obstructions in visual images that may degrade data processing of infrared images. For example, when used on a highway bridge deck, the visual image can be used to identify periodic obstructions from traffic.

Data Processing and Analysis of Sensor Input

The system software analyzes multiple infrared images along with external sensor data (or data received from other source(s) if external sensor(s) are not utilized) in order to detect defects. Data analysis may include determining the log rate of change of each pixel of an infrared image over optimal periods of time identified with the external sensor data. Optimal periods of time may include constant heating and constant cooling periods. Data analysis may include correlating the infrared image data with the external sensor data. Data analysis may further include phase or spectral analysis (e.g., Fast Fournier Transform) of images over time. Data analysis may further include a selection of a single optimal infrared image from the entire collection of infrared images that best represents an internal defect. Data analysis may further include any other suitable processing method that uses the infrared, visual, and external sensor data.

Defect Detection

Software components may analyze processed infrared images in order to extract defects. Defect detection components may determine the size and spatial location of the defect. Defect detection may be correlated with visual image surface indication identification such that internal defects may be separated from surface indications.

Depth Measurement

Software components may analyze processed or unprocessed images in order to determine the depth of a defect.

Data Archive

A software component archives all data collected. This includes the raw image data, external sensor data, and the processed data. Data archiving provides layers of data access that prevents changes to the original raw data in order to provide a certifiable, traceable data set.

Report Output

A software component may create custom-made reports for the end user. The reports may include all processed data and images showing defects and location of defects.

Examples of Operation and Measurement

The following describes how the system and method of the invention may be used in different applications.

Highway Bridges

Figure 5:
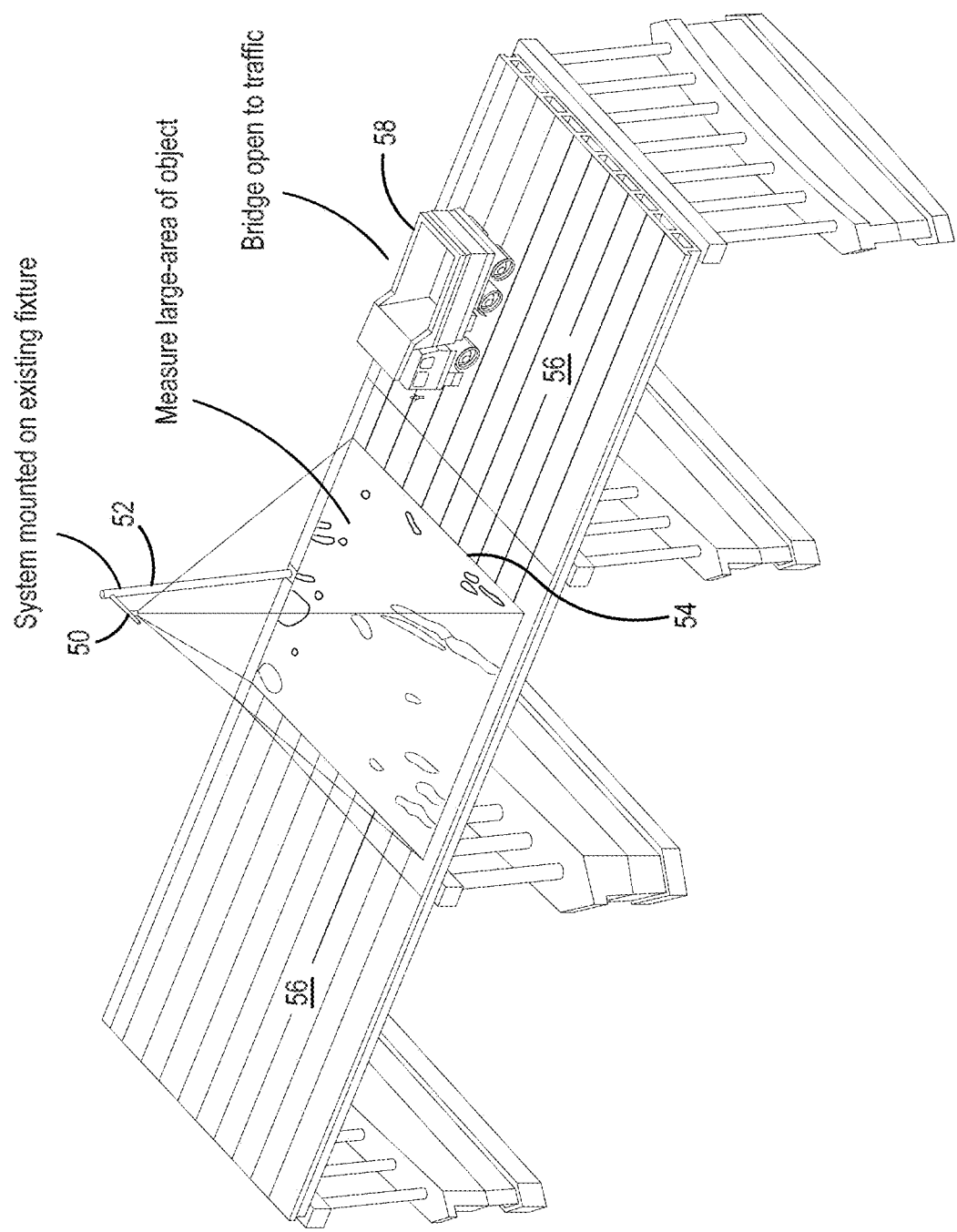
FIG. 5 shows one embodiment of positioning a system of the invention for measuring a highway bridge deck while the bridge deck is open to traffic.

The following describes how the system and method may be used to measure a highway bridge deck. The general concept of this application is shown in FIG. 5. In this case, the system 50 is installed on an existing light fixture 52 with a field-of-view over a large area 54 of the bridge deck 56. The system will make measurements of the bridge deck over time while the bridge deck is open to unobstructed traffic 58. The measurements will be based on data obtained through the infrared camera(s), visual camera(s) and external sensors provided.

Figure 6A:
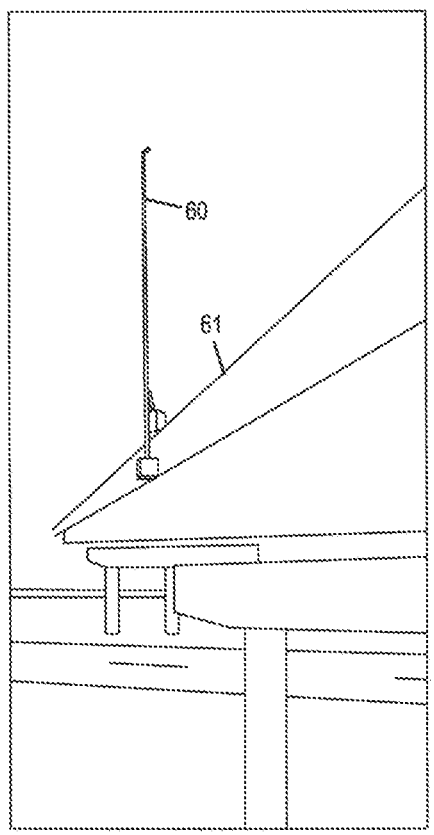
FIGS. 6a and 6b show two embodiments for mounting a system of the invention on a bridge.
Figure 6B:
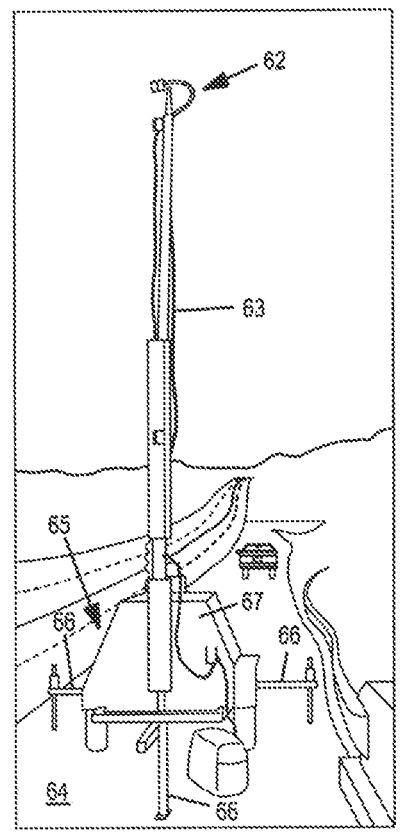

The system may be installed on an existing fixture at the bridge, such as a sign support or light pole, or arranged on a portable mast that is positioned at the bridge but out of the flow of traffic (in the shoulder or median of the bridge). Two possible installation options for a highway bridge are shown in FIGS. 6a and 6b. FIG. 6a shows components of the system arranged on a mast 60 affixed to a bridge 61. FIG. 6b shows components 62 (camera head and pan tilt unit) of the system mounted on a movable, in this instance towable, mast 63 positioned on a surface 64 adjacent an area to be measured. In FIG. 6b, the towable trailer 65 includes stabilizers 66. A power source may be included in the body 67 of the trailer, as well as other components of the system. A camera head of the system may also be mounted on a small balloon (not shown) that is tethered to a structure or other fixed or unsecured aerial platform. An example of an unsecured aerial platform is a drone. These types of structure will enable the camera head to be placed at a much greater height than a mast. The movement of the balloon or other aerial platform would be eliminated from images with the use of spatial reference targets mounted to the bridge.

The camera head is to be mounted at a location that enables a field-of-view of the areal section of a bridge deck that is of interest for measurement. Once set up at a desired site, the operator of the system then orients the pan tilt unit to define multiple measurement locations. The operator configures the measurement parameters, which may include the start time, stop time, and data collection intervals. The operator then initiates data collection. The system automatically collects multiple infrared and visual images at the operator specified intervals. The bridge structure is open to traffic and the system data collection does not interfere with normal operation of the bridge. While collecting images, the system may automatically transfer images to a remote site for data backup and/or offsite data processing.

Figure 7:
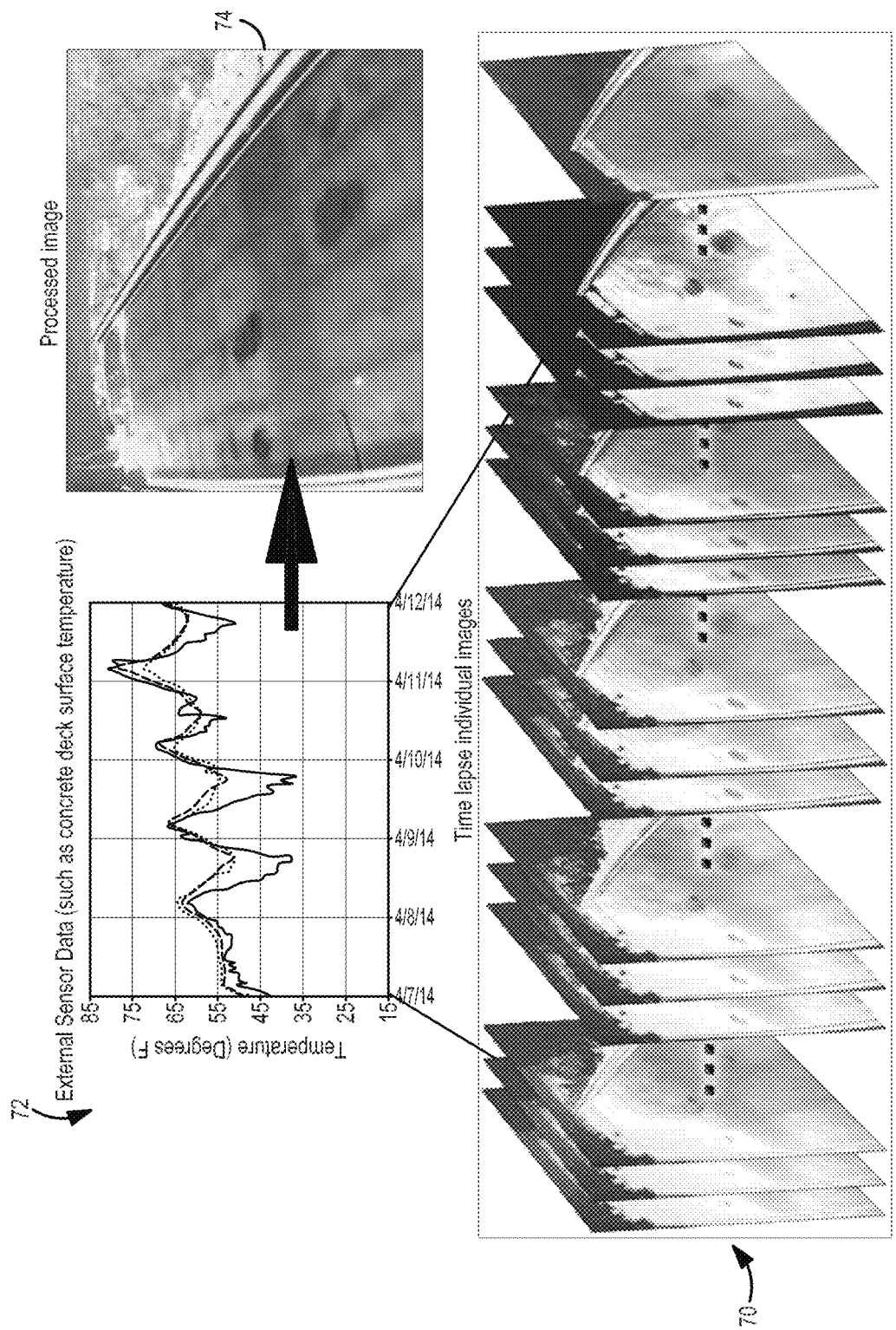
FIG. 7 schematically shows multiple infrared images being combined with external sensor data to produce a processed image showing a defect.

FIG. 7 shows a schematic of multiple infrared images 70 being combined with external sensor data 72, which in this case is the surface temperature of the bridge deck, in order to produce a processed defect image 74.

Figure 8A:
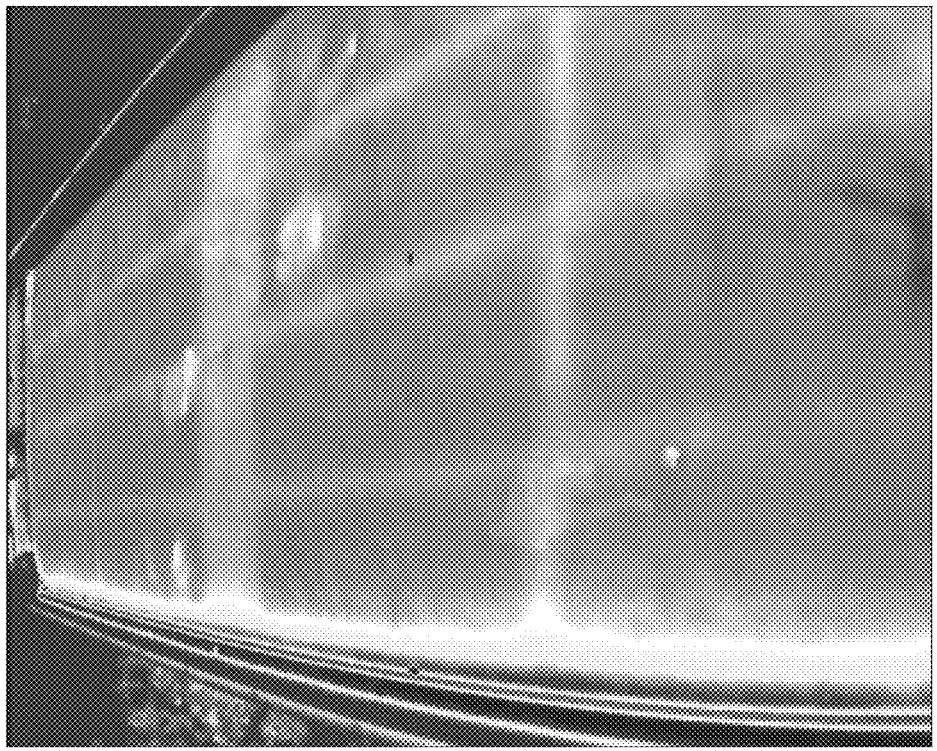
FIGS. 8a and 8b show a comparison of a conventional single frame infrared image (FIG. 8a) and a time lapse image of the system and method of the invention (FIG. 8b) whereby the increased clarity of defect measurement and detection of the inventive system and method is evident.
Figure 8B:
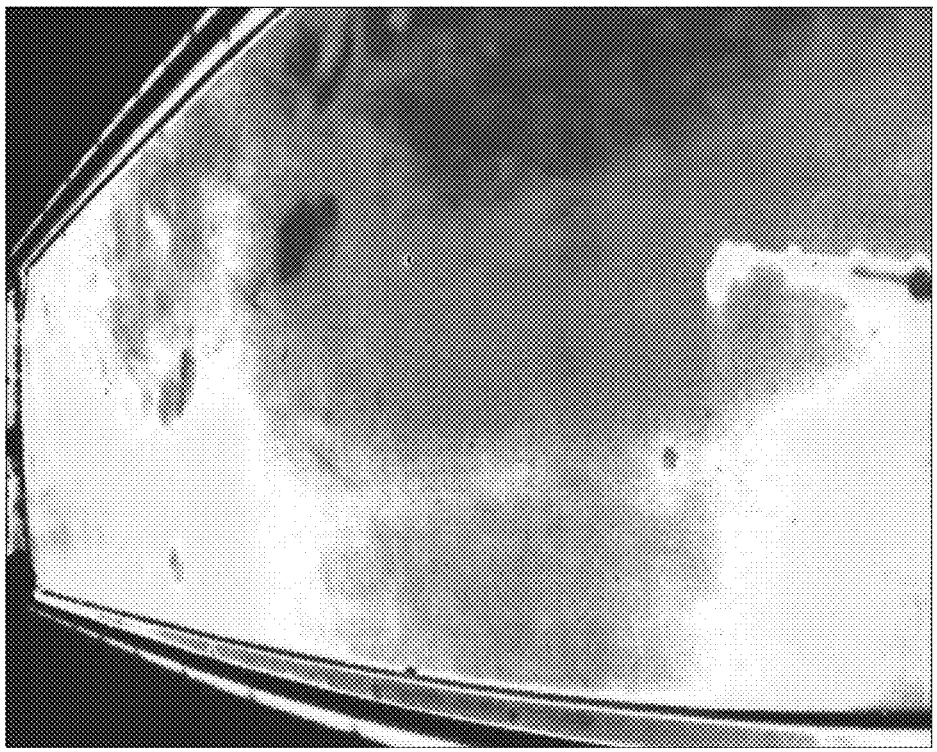

FIGS. 8a and 8b show a comparison of a conventional single frame infrared image (FIG. 8a) taken at the best possible instant in time to an image created with the system of the invention (FIG. 8b) showing increased defect measurement and detection of structural features below the bridge deck (beams and diaphragms).

Figure 9B:
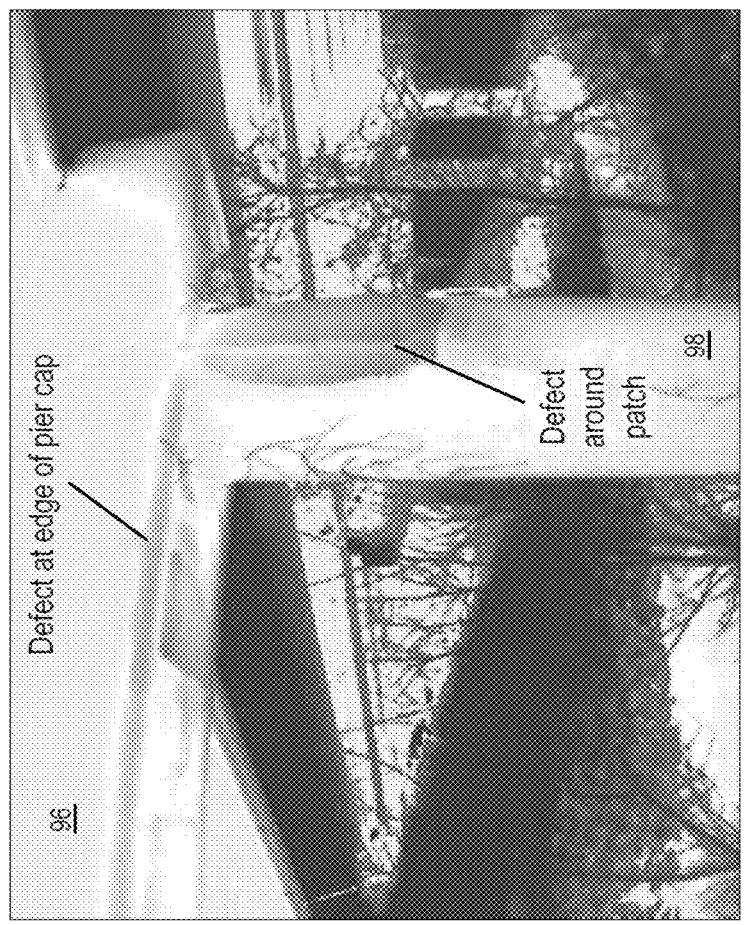
FIG. 9b is an image provided by the system of FIG. 9a showing defects in the pier cap and column.
Figure 9A:
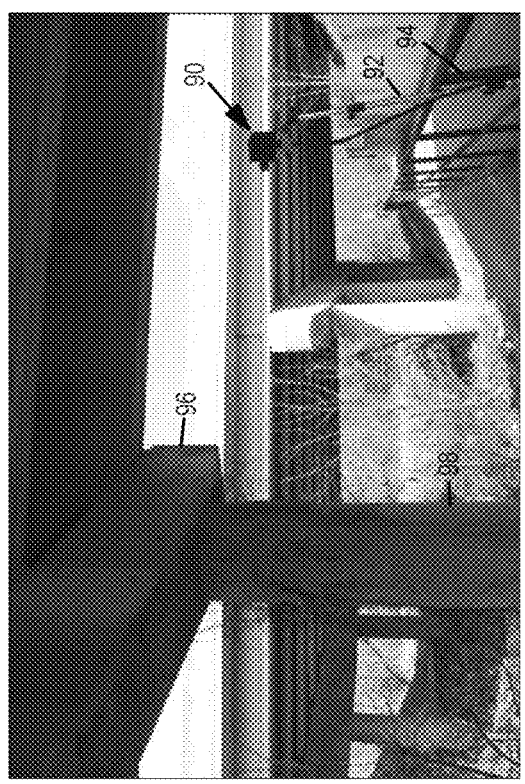
FIG. 9a shows components of the system of the invention positioned under a bridge to measure a pier cap and column of the bridge.

The system of the invention may be used on the substructure of a bridge or the underside (soffit) of a bridge deck. The system may be used to measure such components as piers, columns, pier caps, piles, beams, concrete beams, abutments, or other components. FIGS. 9a and 9b show components 90 (camera head and pan tilt unit) of the system of the invention mounted on a pole of an adjustable height 92 attached to a fence 94 used to measure a pier cap 96 and a column 98 under a bridge. FIG. 9b shows the infrared image of the pier cap 96 and column 98 following measurement and analysis showing defects detected therein. FIGS. 10a and 10b show components of the system of the invention used to measure the soffit (underside) of E bridge. FIG. 10a shows a camera head 100 of the system positioned in relation to the underside area 102 of a bridge to be measured. FIG. 10b shows the infrared image of the underside of the bridge following the measurement and analysis.

The invention provides for measurements on concrete objects, but may also work on other materials that include, but are not limited to, composites, wood, masonry, or other typical building materials.

Examples of System and Method Used with Ship Wearing Surface

The following describes how the system and method of the invention are used to measure a protective wearing surface on a naval vessel, such as an amphibious assault ship or an aircraft carrier. Many military vessels have surfaces which can over time develop defects therein, such as aircraft carriers which have, for example, a wearing surface on the flight deck to aid in operation of aircraft. This wearing surface is typically bonded to the surface (e.g., an epoxy-based coating) or can be a metalized coating (e.g., a thermal spray coating). In both cases, the bond of the wearing surface is critical to proper ship operation and aircraft safety. The system and method of the invention can detect defects or non-visible damage in this wearing surface over areas of substantial size and, in many cases, without affecting operation of the ship.

The general operation of the system and method in relation to a wearing surface of a naval vessel is very similar to the highway bridge example above. System components are installed on an existing structure of the ship or a dedicated mounting location is created. An example of system arrangement for measurement of a ship's wearing surface is shown in FIG. 11. A camera head on a pan tilt unit is mounted on a structural feature of the ship, or may be arranged on a portable mount, that enables a field-of-view of the section of ship deck that is of interest for measurement. Once arranged at the site, an operator then orients the pan tilt unit to define multiple measurement locations. The operator configures the measurement parameters that include the start time, stop time, and data collection intervals. The operator then initiates data collection. The system automatically collects multiple infrared images and multiple visual images at the operator specified intervals. Data from external collection sources, such as sensors, is also collected, e.g., surrounding environmental conditions, such as air and surface temperatures, wind speed, and solar radiation. While collecting images and other data from sensors and/or other sources, the system may automatically transfer images to a remote site for data backup and/or offsite data analysis.

In addition to internal defects in the wearing surface, including the bonding layer, the system and method can also detect small debris or objects on the wearing surface, often referred to as Foreign Object Debris (FOD). FOD present on a flight deck may damage an aircraft or may cause other unwanted negative effects. The system and method can identify FOD on a flight deck over a very large area.

Example of System and Method Used with Building Applications

The system and method of the invention may be used for the measurement of building interiors or exteriors. Conventional hand-held infrared thermography is currently used in this application to detect heat loss or other structural defects (e.g., internal water leaks). Conventional infrared thermography suffers from the inability to separate emissivity difference from temperature difference and may often result in inaccurate measurements. The system and method of the invention can reduce or eliminate the sensitivity of the measurement to emissivity differences by processing multiple images taken over an extended period of time, thereby improving measurement quality and providing the opportunity to detect more defects.

Examples of Other Applications

The system and method of the invention may be used on many other objects and the above examples are not exhaustive. These other items may include other large structures, for example, dams, nuclear containment structures, or retaining walls. The system and method of the invention may be used in many applications where conventional handheld infrared thermography is currently used in order to provide greater and more accurate measurements.

Table 1 below sets forth the basic steps of a presently preferred operation of the system and method of the invention.

TABLE 1

A. Installation of system.
   (1) Selection of a suitable installation location; and
   (2) Installation of the system components [main instrument/computer, camera head(s), power (battery) system, wireless antenna, external wireless sensor(s)].
B. Perform set up arrangement.
   (1) Placement of wireless external sensor(s) on the object;
      (a) System collection of sensor data during measurements;
   (2) Defining multiple measurement positions when using a pan tilt unit; and
   (3) Defining measurement parameters (start time, stop time, data collection intervals, etc.).
C. Initiation of data collection.
   (1) Automatic collection of infrared images and visual images by system components, as well as automatic collection of external sensor data; and
   (2) Optionally, automatic transfer of data to a remote site during collection.
D. Data collection occurring over an extended period of time that is sufficient for the object being measured to experience at least one period of thermal change (i.e. one day/night cycle of heating and cooling); but preferably multiple days/weeks of operation to increase data available for processing and analysis.
   E. Data collection is completed.
   F. Locking raw data file to prevent any changes.
   G. Data Processing.
      (1) Software components process data to stabilize images;
      (2) Software components process data to stitch together multiple images;
      (3) Software components analyze visual images to identify surface features;

TABLE 1-continued (4) Software components analyze visual images to detect periodic interferences;
(5) Software components process data to analyze multiple images to detect defects using external sensor data;
(6) Software components detect defects; and
(7) Software components measure defect depth.
H. Report creation.
(1) Software components create custom-defined reports with measurement data.

The exemplary embodiments disclosed herein are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention.

It is claimed:

1. A system for detecting and measuring one or more internal defects in a large-scale object comprising
   (a) one or more camera heads including at least an infrared camera and, optionally, a visual camera;
   (b) at least one environmental data collection source adapted to identify one or more environmental parameters, which may be the same or different from said infrared camera; and
   (c) an embedded computer adapted to control said infrared camera and said visual camera so that each provides multiple time-lapse images over a pre-determined time period during which the object experiences at least one period of thermal change, and further adapted to receive said multiple time-lapse images and receive data from said at least one environmental data collection source collected over said pre-determined period of time;
   wherein said multiple time-lapse images are of a field-of-view of the object so that said multiple time-lapse images can directly or nearly directly overlay each other;
   wherein internal defects are substantially subsurface within the object and either are nonvisible or substantially nonvisible;
   wherein said system includes a mounting structure to mount the one or more camera heads on or near an object to be measured and to position said one or more camera heads at a height sufficient to obtain a field of view of an area of said object to be analyzed to detect spatial location and depth of one or more internal defects in said object in the field of view.

2. The system of claim 1 wherein each of said one or more camera heads includes an infrared camera and a visual camera.

3. The system of claim 1 further comprising a pan tilt mechanism adapted to orient, through said embedded computer, said one or more camera heads into different measurement locations.

4. The system of claim 2 further comprising a pan tilt mechanism adapted to orient, through said embedded computer, said one or more camera heads into different measurement locations.

5. The system of claim 1 wherein said at least one environmental data collection source is at least one external sensor that collects data over time.

6. The system of claim 1 further comprising a user interface for setup and operation of said system.

7. The system of claim 1 wherein said mounting structure is constructed to provide attachment to (a) an existing part of said object, (b) a movable mast, (c) a mast fixed to the object, (d) a structure adjacent to the object, (e) a balloon tethered to a fixed location on or adjacent to said object, or (f) a movable aerial platform.

8. The system of claim 1 comprising a plurality of said camera heads wherein said plurality of said camera heads is connected to or managed by said embedded computer.

9. The system of claim 1 further comprising an embedded wireless modem for transfer of data from said embedded computer to a remote computer for data storage and/or data processing.

10. The system of claim 1 wherein said one or more environmental parameters include one or more of surface temperature of the object, wind speed, and solar radiation.

11. The system of claim 1 further comprising a calibration specimen separate from the object being measured containing internal defects of known spatial location and depth for placement in the field of view of said one or more camera heads.

12. The system of claim 1 wherein said object comprises a substantially concrete structure.

13. The system of claim 1 wherein said object is a bridge.

14. The system of claim 1 wherein said object is a naval vessel.

15. The system of claim 1 wherein said object is a building.

16. A method of measuring an area of a large-scale object to detect and measure one or more internal defects in said object, said method comprising
   (a) collecting multiple time-lapse infrared images, or multiple time-lapse infrared images and multiple time-lapse visual images, of a predetermined area of said object and collecting environmental data over time for ambient environment of said object, wherein said multiple time-lapse infrared images and said multiple time-lapse visual images are collected at discrete intervals over a predetermined period of time during which the object experiences at least one period of thermal change and said environmental data is collected for at least said discrete intervals over said predetermined period of time, wherein said multiple time-lapse images are of a field-of-view of the object so that said multiple time-lapse images directly or nearly directly overlay each other;
   (b) processing said multiple time-lapse infrared images and said multiple time-lapse visual images and said environmental data to determine a flow of heat through said predetermined area of said object in a manner to detect one or more internal defects;
   (c) in said processing, minimizing or eliminating variations which interfere with detecting and measuring said one or more internal defects in said predetermined area; and
   (d) extracting from said processing at least spatial location and depth of said one or more internal defects in said predetermined area of said object.

17. The method of claim 16 wherein said variations minimized or eliminated in said processing include one or more of emissivity in a measurement, surface anomalies, and periodic obstruction in said infrared images.

18. The method of claim 16 wherein type of said one or more internal defects are identified based on thermal signature.

19. The method of claim 16 further comprising including in (a) in relation to said object, a calibration specimen containing internal defects of known spatial location and known depth; and during said processing using data collected based on said calibration specimen to calibrate measurements on detected defects in said object.

20. The method of claim 16 wherein steps of said method do not interfere with use of said object.

21. The method of claim 16 wherein the object comprises a substantially concrete structure.

22. The method of claim 16 wherein the object is a bridge.

23. The method of claim 16 wherein the object is a naval vessel.

24. The method of claim 16 wherein the object is a building.

* * * * *